United States Patent [19]

Foslien et al.

[11] Patent Number: 5,083,695
[45] Date of Patent: Jan. 28, 1992

[54] STAPLER AND FIRING DEVICE

[75] Inventors: Floyd Foslien, Hudson, Wis.; Alan K. Plyley, Santa Barbara, Calif.; John M. Barker, Ventura, Calif.; Claude Vidal, Santa Barbara, Calif.

[73] Assignee: Minnesota Mining and Manufacturing Company, St. Paul, Minn.

[21] Appl. No.: 629,142

[22] Filed: Dec. 18, 1990

[51] Int. Cl.[5] .......................................... A61B 17/068
[52] U.S. Cl. .......................................... 227/8; 227/19; 227/175
[58] Field of Search ................ 227/8, 19, 175, 178, 227/180, 901

[56] References Cited

U.S. PATENT DOCUMENTS

| | | | |
|---|---|---|---|
| 4,086,926 | 5/1978 | Green et al. | 128/334 R |
| 4,202,480 | 5/1980 | Annett | 227/8 |
| 4,442,964 | 4/1984 | Becht | 227/8 |
| 4,520,817 | 6/1985 | Green | 128/305 |
| 4,633,861 | 6/1987 | Chow et al. | 128/305 |
| 4,633,874 | 6/1987 | Chow et al. | 128/334 R |
| 4,863,088 | 9/1989 | Redmond et al. | 227/19 |
| 4,869,415 | 9/1989 | Fox | 227/19 |
| 4,892,244 | 1/1990 | Fox et al. | 227/8 |
| 4,938,408 | 7/1990 | Bedi et al. | 227/8 |
| 4,951,861 | 8/1990 | Schulze et al. | 227/8 |
| 4,955,959 | 9/1990 | Tompkins et al. | 227/178 |

FOREIGN PATENT DOCUMENTS 0373762 11/1988 European Pat. Off. .
2744824 2/1980 Fed. Rep. of Germany .

OTHER PUBLICATIONS

Flickinger et al., Surgical Stapling *Gastric and Small Bowel Procedures*, pp. 1-145.
Anderson et al., Surgical Stapling *Thoraci, Vascular and Esophageal Procedure*, pp. 1-101.
Brolin et al., Surgical Stapling *Bariatric Procedures for Morbid Obesity*, pp. 1-115.

Primary Examiner—Frank T. Yost
Assistant Examiner—Scott A. Smith
Attorney, Agent, or Firm—Gary L. Griswold; Walter N. Kirn; Jeffrey J. Hohenshell

[57] ABSTRACT

An improved stapler firing assembly and a surgical stapler are disclosed. The stapler comprises structural members having handle parts with opposite sides and jaw parts projecting from the handle parts. The stapler includes a mechanism for releasable engagement between an elongate locking member and the structural members comprising a lever lock including a hook portion adapted to pass through a slot in a handle part. The lever lock is mounted on the locking member and includes first and second release buttons and actuating means mounting the first and second release buttons on opposite sides of the locking member for movement between first and second positions with respect to the locking member. The stapler firing assembly comprises a pusher adapted to move longitudinally along one of the jaw parts to sequentially press the staples against an anvil. There is also present a firing handle body having opposite end portions and a mechanism mounting the handle body on the pusher for movement relative to the pusher between a first position and a second position so that the firing handle body can be positioned to be manually engaged on either side of the handle parts to move the second end of the pusher along the second jaw to eject and close the staples.

4 Claims, 3 Drawing Sheets

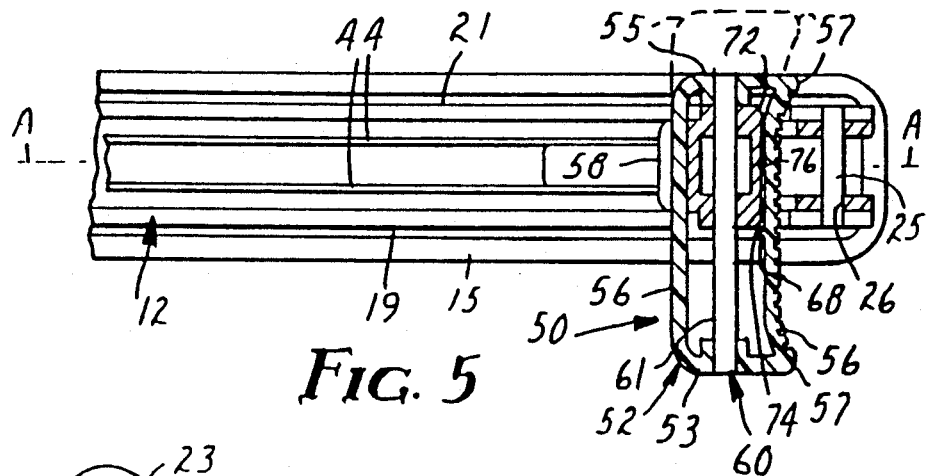
FIG. 5
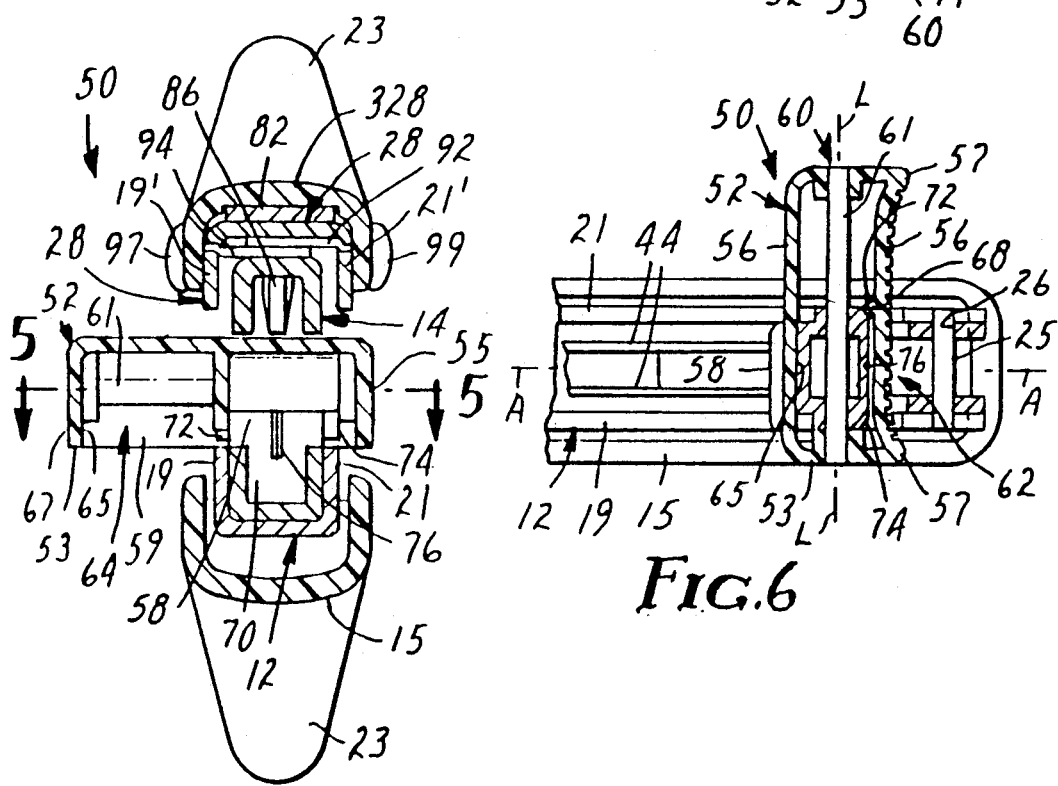
FIG. 4
FIG. 6

STAPLER AND FIRING DEVICE

TECHNICAL FIELD

The present invention relates generally to surgical stapling instruments for applying parallel rows of staples through compressed living tissues.

BACKGROUND

The art is replete with surgical stapling instruments used for applying parallel rows of staples through compressed living tissue. These types of stapling devices are used, for example, in transecting or reconnecting intestinal, gastric and lung tissue.

One known surgical stapling instrument of this type is well known and is currently available under the trade designation "The ILA Stapler", catalog #3957 by Minnesota Mining and Manufacturing Company, St. Paul, Minn. The use of the stapler is described in the publication entitled "Surgical Stapling, Gastric and Small Bowel Procedures, Volume I", ISBN 0-937433-00-4, Library of Congress Catalog Number 85-082599 available from Minnesota Mining and Manufacturing Company, St. Paul, Minn. the contents of which is expressly incorporated herein by reference. The ILA Stapler and an improvement thereto is described in Redmond et al., U.S. Pat. No. 4,863,088 the entire specification of which is also herein expressly incorporated by reference. That stapling instrument comprises first and second elongate structural members each comprising a handle part and a jaw part projecting from a first end of the handle part. The structural members have pivot means at second ends of their handle parts adapted for free engagement and disengagement in a plane normal to the directions in which the members are elongate, which pivot means afford, when engaged, relative pivotal movement of the structural members in the plane between a closed position with the jaw parts in closely spaced relationship, and an open position spaced farther from each other than in the closed position. An elongate locking member having a pivot point closely adjacent a first end is mounted at its pivot point on the first end of the second structural member for pivotal movement around an axis generally normal to the plane between a locking position generally aligned with the handle part of the second structural member, and a release position with a second end of the locking member spaced from the second end of the second structural member. The first end of the locking member and the handle part of the first structural member adjacent its first end have surfaces adapted, when the pivot means are engaged and the structural members are in their open position, for engagement during movement of the locking member from its release position to its locking position to forcefully move the structural members to their closed position so that high compressive forces can be applied on tissues to be stapled between the jaw parts of the structural members. The stapler also comprises means adapted for releasable engagement between the elongate locking member and the second structural member which releasably hold the locking member in its locking position and thus maintain any compressive forces applied between the jaw parts. The stapling instrument is adapted to have a fixed or removable anvil positioned along one of the jaw parts, and a cartridge containing a plurality of staples disposed in rows positioned along the other of the jaw parts in opposition to the anvil, and the cartridge includes manually actuatable means for sequentially ejecting the staples from the cartridge to press the staples against the anvil to engage and close the staples in tissues between the jaw parts when the structural members are in their closed position. Additionally, if desired, the cartridge can include a knife that moves along and bridges between the cartridge and anvil to cut tissues between the rows of applied staples.

Existing "ILA" type staplers include a firing handle located on only one side of the surgical stapler handle along with a relatively large size jaw and a relatively small size jaw. These types of staplers and cartridge assemblies encounter problems when they are used in a medical procedure at a location in the patient's body where there is little room or clearance to maneuver or orient the surgical stapler. For example, in some procedures, the relatively small size jaw is placed through a slit-like incision in bowel tissue in order to be positioned adjacent to tissue to be stapled, and the larger jaw is placed through another slit-like incision in other bowel tissue. It is preferable to make these apertures as small as possible to minimize damage to the tissue. Existing staplers include a firing handle located only on one side of the surgical stapler and, since the position of the firing handle is dependent upon the location of the small jaw, the resulting position of the stapler is sometimes one in which access to the firing handle is restricted or even blocked by tissue (e.g. an organ). Thus, it is difficult for the surgeon to manually fire the stapler using the firing handle due to the obstructing tissue. Heretofore, attempts to solve this problem include using a long cylindrical rod placed against the firing handle to fire the stapler, but this is an undesirable solution as the use of such a rod for that purpose reduces the control the surgeon has over the firing of the stapler and creates a danger that the rod would slip off the firing handle and damage internal tissues.

Another problem associated with "ILA" type staplers is also encountered when the stapler is used in a surgical procedure at a cramped location where the surgeon's capacity to position the stapler is restricted due to the proximity of the stapler to sensitive tissue. Once the stapler has been oriented in the proper position, existing staplers use a lever locking member to clamp or approximate the tissue to be stapled between the stapler jaws prior to firing. Once the stapler is fired, existing lever locking members, such as the "ILA" stapler disclosed in U.S. Pat. No. 4,863,088 to Redmond et al., release the locking member by means of a button located on only one side of the stapler. Again, access to the button may be restricted or difficult if the stapler is used at a location in close proximity to sensitive tissue.

U.S Pat. No. 4,633,874 to Chow et al. discloses a latching mechanism including a latch arm which is movable to a partially latched position in which the jaw members are loosely connected together to permit the staple cartridge and anvil to be adjusted in position on the tissue without disconnecting the jaw members from each other. U.S. Pat. No. 4,520,817 to Green discloses a locking handle pivotable to cause camming surfaces to slide on lugs to thereby rotate frames toward each other about a pivot bar between open and closed positions. The prior art staplers disclosed in Chow et al. and Green disclose a locking mechanism generally referred to as an "over center" link and it is believed that such over center links are difficult to open when the stapler is used with thick tissue. Problems associated with opening the locking mechanism are only aggravated when the stapler is used at a cramped location.

DISCLOSURE OF THE INVENTION

The present invention provides an improved surgical stapler cartridge assembly including a firing handle assembly which affords firing of the stapler from either side or from both sides of the handle, and an improved surgical stapler including dual-sided lever lock release for releaseably locking an elongate locking member which affords release of the locking member from either side of the stapler handle. The present invention may also be expressed as a combination of the improved firing handle assembly with the improved surgical stapler. These features create a stapler which is particularly suitable for convenient use in medical procedures in remote, cramped conditions.

According to the present invention there is provided an improved surgical stapler which like the ILA stapler described above has first and second structural members each being elongate in a first direction. The first structural member has a handle part having first and second ends, the second structural member has a base portion having first and second ends, and each of the structural members having a jaw part projecting from its first ends. The jaw parts have proximal ends adjacent the first end of the handle part of the first structural member and the first end of the base portion of the second structural member, and each of the jaw parts have distal ends remote from the proximal ends.

The structural members have pivot means at their second ends adapted for free engagement and disengagement in a plane normal to the first direction for affording, when engaged, relative pivotal movement of the structural members in the plane between a closed position with the jaw parts in closely spaced relationship, and an open position with the jaw parts spaced farther from each other than in the closed position. In the closed position, the handle part of the first structural member and the base portion of the second structural member define a space between the structural members over the majority of the distance between the first and second ends. An elongate locking member is present which has first and second ends and a pivot point closely adjacent the first end of the locking member. The pivot point of the locking member is mounted on the second structural member adjacent the first end of the second structural member for pivotal movement around an axis generally normal to the first direction between a locking position generally aligned with the base portion of the second structural member, and a release position with the second end of the locking member spaced from the second end of the second structural member. The first end of the locking member and the handle part of the first structural member adjacent the first end of the first structural member have surfaces adapted, when the pivot means are engaged with the structural members in the open position, for engagement during movement of the locking member from the release position to the locking position to forcefully move the structural members to the closed position. There is also provided means for releasable engagement between the elongate locking member and the second structural member for holding the locking member in the locking position.

Unlike the ILA stapler described above, however, the means for releasable engagement between the elongate locking member and the second structural member for holding the locking member in the locking position comprises a dual-sided lever lock release. The dual-sided lever lock release comprises surfaces in the second structural member defining a slot generally adjacent the second end of the second structural member, and a lever lock having a retaining surface adapted to engage the surfaces defining the slot of the second structural member to retain the elongate locking member in the locking position. The lever lock is adapted to move between an unlatched position to afford movement of the elongate locking member to the release position and a latched position to retain the elongate locking member in the locking position The dual-sided lever lock release includes a pair of release arms actuatable from either side of the lever cover for independently moving the lever lock from the latched position to the unlatched position so that a surgeon may release the locking member in cramped conditions.

Also, like the ILA stapler described above, in the surgical stapler according to the present invention, the first structural member is adapted to receive the staple cartridge assembly and the jaw part of the second structural member is adapted to receive an anvil surface. The staple cartridge assembly comprises a cartridge body for enclosing a plurality of staples disposed in rows oriented longitudinally of the jaw part in opposition to the anvil when the structural members are in their closed position. Also, the cartridge assembly includes manually actuatable means including cam-like drivers or pushers adapted to be moved through longitudinal slots in the cartridge body by manually pressing on a firing handle assembly. The pushers sequentially press the plurality of staples within the cartridge body against the anvil to engage and close the plurality of staples in tissues between the jaw parts when the structural members are in the closed position. The pushers are movable in the first direction between a retracted position with the plurality of staples enclosed within the cartridge body and an extended position with the plurality of staples closed within tissue. The firing handle assembly is located within the space between the handle parts and includes a firing body adapted to be manually engaged to afford movement of the pushers between the retracted and the extended positions.

Unlike the previously described ILA stapler, however, in the improved staple cartridge for use in the stapler according to the present invention, the firing body in the firing handle assembly used to manually fire the surgical stapler is elongate and has a longitudinal axis transverse to a direction of elongation of the structural members and is mounted on a firing handle adapter which has surfaces adapted for connecting the firing body to the pushers and also mounts the firing body for releasable lateral movement between at least two firing positions to afford actuation of the pushers from either side of the stapler. Detent surfaces are provided for releasably securing the firing body in a first position located generally on one side of the stapler, a second position generally located on the other side of the stapler and a middle position located on both sides of the stapler. Thus, a surgeon may access the firing body from either side of the stapler which is particularly useful when the stapler is used in cramped conditions.

BRIEF DESCRIPTION OF THE DRAWING

The present invention will be further described with reference to the accompanying drawing wherein like reference numerals refer to like parts in the several views, and wherein:

FIG. 4 is an enlarged sectional view of the stapler and cartridge assembly of FIG. 1 taken approximately along lines 4—4 of FIG. 2;

FIG. 5 is an enlarged partial sectional view of a first assembly of the stapler and the cartridge assembly of FIG. 1 taken approximately along line 5—5 of FIG. 4 and illustrating the position of the firing body in a first position with solid lines and a middle position with broken lines;

FIG. 6 is an enlarged sectional view of the stapler assembly and the cartridge assembly of FIG. 1 which is similar to FIG. 5 but which illustrate the position of the firing body in a second position;

DETAILED DESCRIPTION

Figure 1:
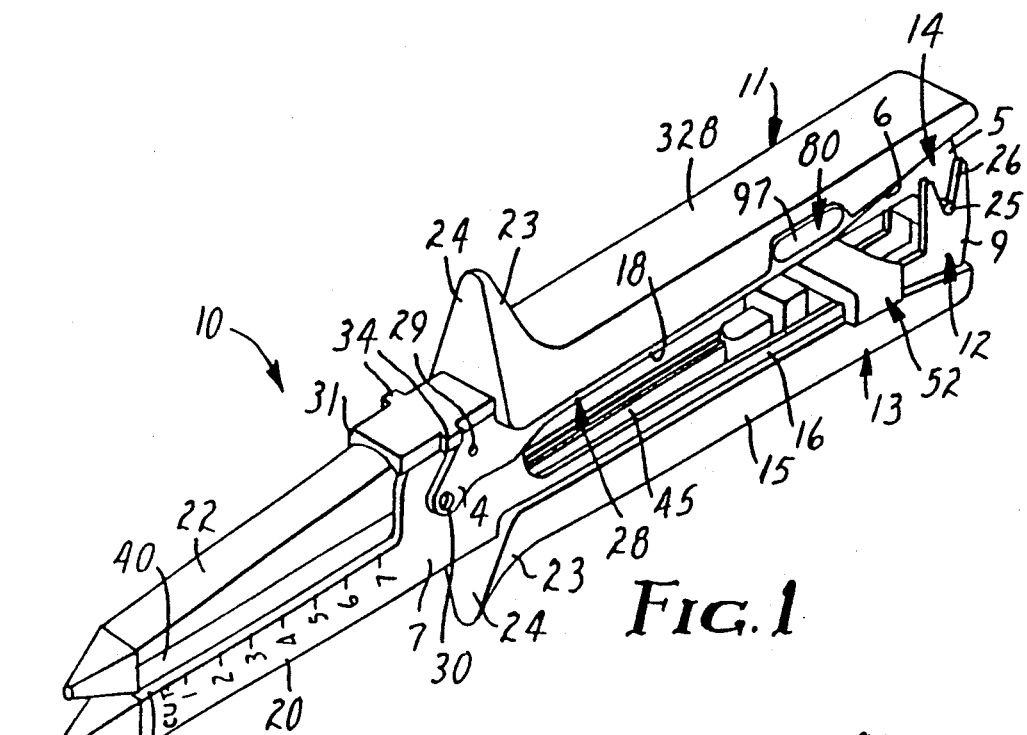
FIG. 1 is a perspective view of a surgical stapling instrument and a cartridge assembly according to the present invention showing first and second assemblies of the stapling instrument in a closed position.

Referring now to the drawing, there is shown a surgical stapling instrument 10 and a cartridge assembly 2 according to the present invention, generally designated by the reference numerals 2 and 10, respectively.

The surgical stapler 10 comprises two separable assemblies 11 and 13 comprising first and second elongate structural members 12, 14. The first and second elongate structural members 12, 14 have first and second sides 19, 21 with the first structural member 12 comprising a handle part 16 and a jaw part 20 projecting from a first end 7 of the handle part 16, and with the second structural member 14 including a base portion 8 and a jaw part 22 projecting from a first end 3 of the base portion 8. A tissue stop surface 31 is attached to the second structural member 14 generally adjacent its first end 3 and is adapted to abut tissue. The tissue stop surface 31 provides means for locating and aligning the stapler jaw parts 20, 22 with respect to the tissue to be stapled.

The structural members 12, 14 have pivot means at second ends 5, 9 of the handle part 16 and the base portion 8 comprising two opposite axially parallel outwardly projecting pins 25 on the second structural member 14 and generally U-shaped journal surfaces 26 on the first structural member 12 adapted and positioned for free engagement and disengagement in a plane normal to the directions in which the structural members 12 and 14 are elongate, which pivot means affords, when engaged, relative pivotal movement of the structural members 12, 14 in the plane normal to the directions in which the structural members 12 and 14 are elongate between a closed position (FIGS. 1 and 2) with the jaw parts 20, 22 in closely spaced relationship, and an open position (FIG. 3) with the jaw parts 20, 22 spaced farther from each other than in the closed position. An elongate locking member 28 having a pivot point at a position closely adjacent a first end 4 of the locking member 28 is mounted by a pin 29 on the first end 3 of the second structural member 14 for pivotal movement around an axis generally normal to the plane between a locking position (FIGS. 1 and 2) generally aligned with the base portion 8 of the second structural member 14, and a release position (FIG. 3) with the second end 6 of the locking member 28 spaced from the second end 5 of the second structural member 14. The elongate locking member 28 includes a handle part 18 and a lever cover 328 is attached to the handle part 18. A lever stop 34 is attached to the second structural member 14 to prevent the locking member 28 from pivoting forward from the open position and pinching tissue.

The first end 4 of the locking member 28 and the first end 7 of the first structural member 12 have surfaces provided by two opposite axially parallel inwardly projecting pins 30 on the handle part 18 and side surfaces of generally U-shaped journal surfaces 32 on the first structural member 12 opening toward the second end 9 of the first structural member 12, adapted, when the pivot means are engaged with the structural members 12, 14 in the open position, for engagement during movement of the locking member 28 from its release position (FIG. 3) to its locking position (FIG. 2) to forcefully move the structural members 12, 14 to their closed position so that high compressive forces can be applied to tissues between the jaw parts 20, 22 of the structural members 12, 14.

A handle cover 15 is attached to the handle part 16 of the first structural member 12. A handle cover 328 is attached to the handle part 18 of the locking member 28 and is similar in shape to the handle cover 15. The handle cover 328 and the handle cover 15 have manually engageable projections 23 having engagement surfaces 24 disposed generally at an included angle of less than ninety degrees with respect to the direction of elongation of the jaw parts 20, 22, preferably eighty-five degrees. The engagement surfaces 24 of the handle cover 328 and the handle cover 15 are adapted to be engaged with the fingers of a user's hand while the thumb of that hand is used to operate an adjustable firing body 50. The angle between the jaw parts 20, 22 and the engagement surfaces 24 is less than ninety degrees to provide grasping means for the user's fingers to provide an incline to prevent the user's fingers from slipping or sliding from the handle covers 15, 328. The handle covers 15, 328 may be constructed from any suitable material such as, but not limited to, polycarbonate or ABS plastic.

Figure 2:
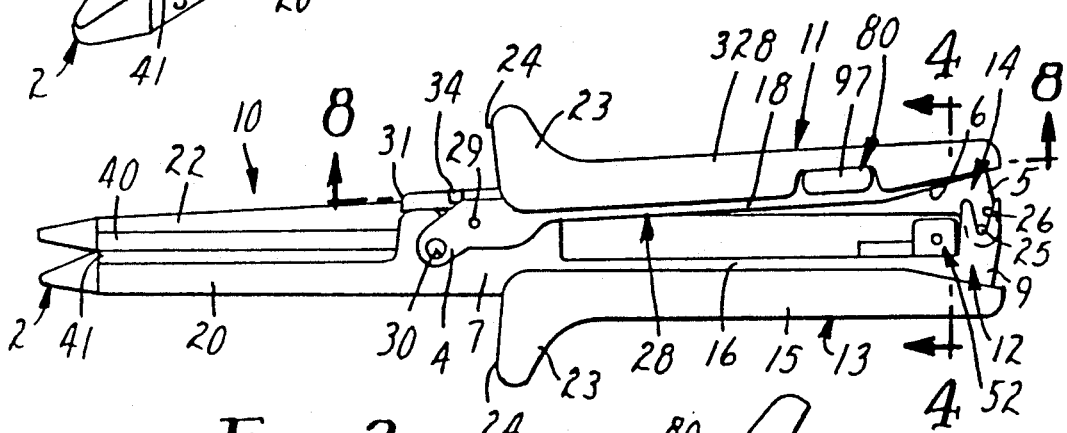
FIG. 2 is a side view of the surgical stapling instrument of FIG. 1.
Figure 3:
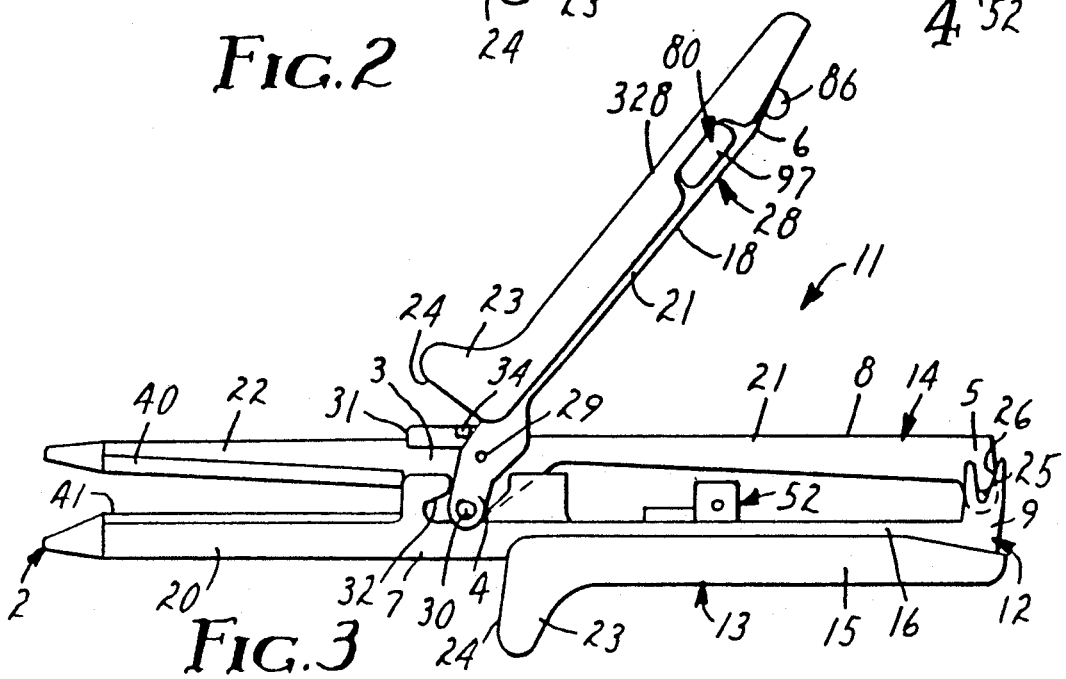
FIG. 3 is a side view of the surgical stapling instrument of FIG. 1 showing the first and second assemblies of the stapling instrument in an open position.
Figure 7:
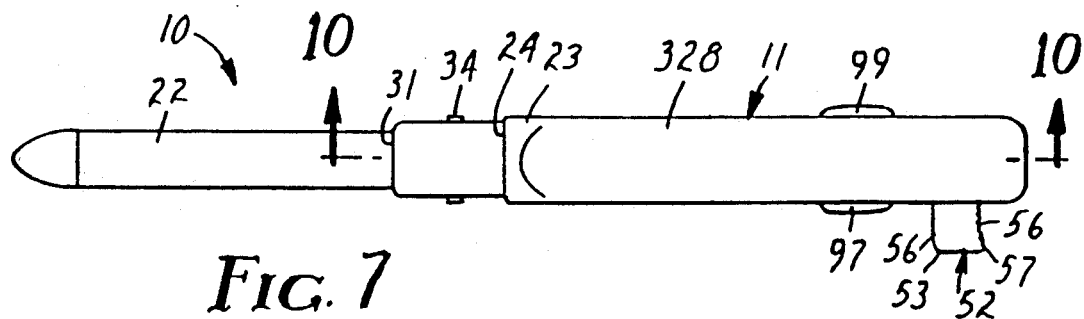
FIG. 7 is a top view of the surgical stapling instrument of FIG. 1.
Figure 8:
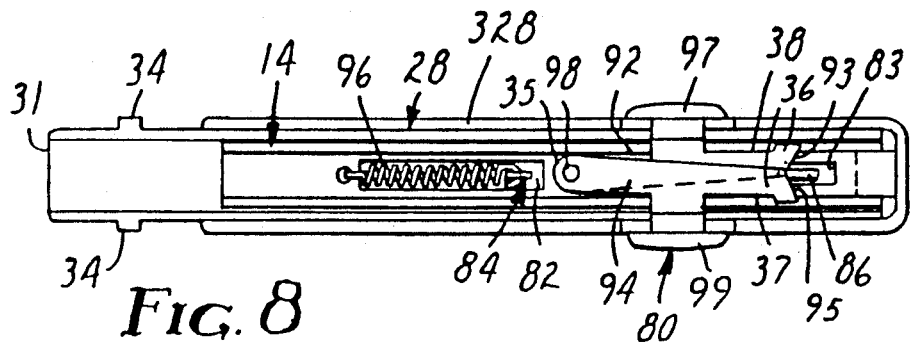
FIG. 8 is enlarged fragmentary sectional view of the surgical stapling instrument of FIG. 1 taken approximately along line 8—8 of FIG. 2 and illustrating a lever lock in a latched position.

A novel structure of the stapling instrument 10 that distinguishes the present invention from known stapling instruments is means for releasable engagement between the elongate locking member 28 and the second structural member 14 generally designated by the reference number 80 which affords release of the locking member 28 from either side 19, 21 of the stapler 10. As shown in FIGS. 7-10, that dual-sided lever lock release assembly 80 comprises surfaces defining a slot 83 in the second structural member 14 adjacent the second end 5 of the second structural member 14 (FIG. 9), and a lever lock 84 having a generally rectangular planar base portion 82 having a longitudinal axis. The base portion 82 is located within a chamber 81 between the handle part 18 and the lever cover 328, and a hook portion 86 is connected to the base portion 82 by being integral therewith. The hook portion 86 projects generally normally from the base portion 82 and has a retaining surface 87 adapted to engage a surface adjacent one end of the slot 83 of the second structural member 14 to retain the elongate locking member 28 in the locking position (FIG. 10). The lever lock 84 is adapted to move axially between an unlatched position (FIG. 9) to afford movement of the elongate locking member 28 to the release position (FIG. 3) and a latched position (FIGS. 8 and 10) to which the lever lock 84 is biased by a spring 96 to retain the elongate locking member 28 in the locking position (FIG. 2). The handle part 18 of the elongate locking member 28 has surfaces defining an aperture 88 communicating with the chamber 81 and located generally adjacent the second end 6 of the elongate locking member 28 which affords passage of the hook portion 86.

The dual-sided lever lock release 80 is located on first and second sides 19,, 21' of the elongate locking member 28 and comprises first 92 and second 94 release arms each having first and second ends 35, 36, and first and second opposite side surfaces 37, 38. The second ends 36 of the release arms 92, 94 include camming surfaces 93, 95; and the first ends 35 of the release arms 92, 94 are pivotally attached to the handle part 18 of the elongate locking member 28 by a pin 98 to afford movement between an engaged position (FIG. 9) with camming surface 93 or 95 in engagement with the lever lock 84 to unlatch the lever lock 84 and a disengaged position (FIG. 8) with the camming surface 93 or 95 disengaged or spaced from the lever lock 84. Preferably the release arms 92, 94 are constructed to remain slightly engaged with the lever lock 84 when they are in the disengaged position to prevent the camming surfaces 93 or 95 from sliding out of contact with the lever lock 84.

Figure 9:
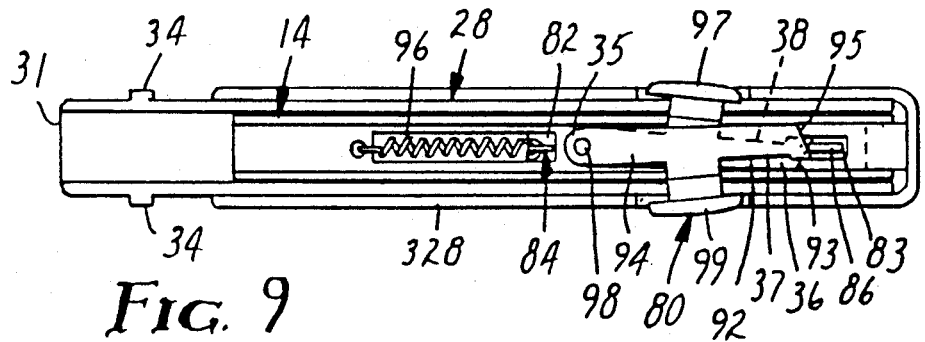
FIG. 9 is an enlarged fragmentary sectional view of the surgical stapling instrument and cartridge assembly of FIG. 1 which is similar to FIG. 8 except that FIG. 9 illustrates the lever lock in an unlatched position.
Figure 10:
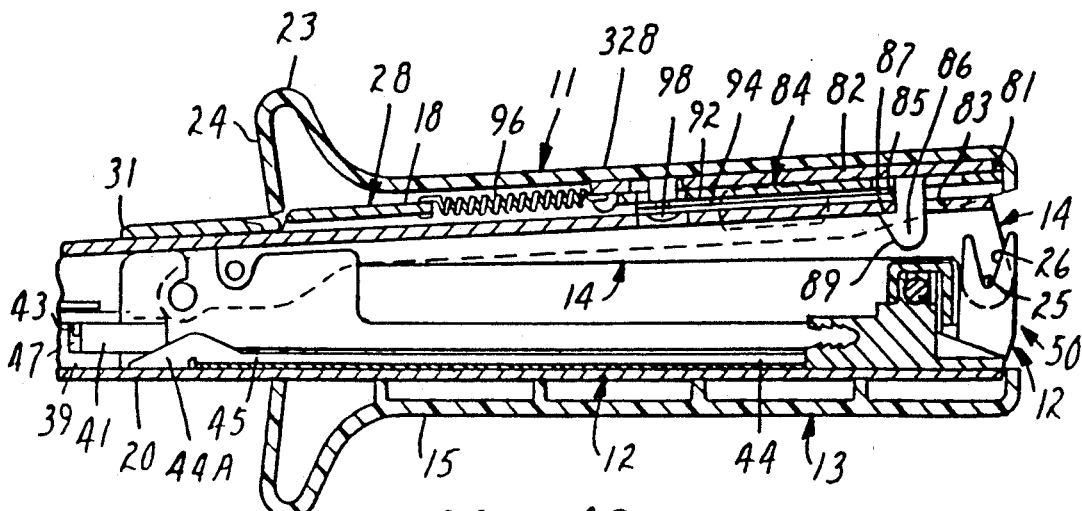
FIG. 10 is an enlarged fragmentary sectional view of the surgical stapling instrument and the cartridge assembly of FIG. 1 taken along line 10—10 of FIG. 7 and illustrating the lever lock in a latched position and having portions broken away to show detail.

The lever lock 84 includes a shoulder surface 85 adjacent the hook portion 86 for receiving the camming surfaces 93, 95 when either of the release arms 92 or 94 are moved to the engaged position (FIG. 9). The release arms 92, 94 move independently of each other and thus, although FIG. 9 shows both release arms 92, 94 moved to the engaged position, the user need only actuate one of the release arms 92 or 94 to release or unlatch the lever lock 84 from the second structural member 14. This feature affords independent release of the elongate locking member 28 from either of its sides 19', 21' and provides an alternative release means when using the stapler in a cramped area.

First and second release buttons 97, 99 are mounted on the release arms 92, 94 adjacent the sides 19', 21' of the elongate locking member 28 for movement between first (FIG. 8) and second (FIG. 9) positions with respect to the locking member 28. The first button 97 is mounted to the second release arm 94 along its first side 37 and the second button 99 is connected to the first release arm 92 along its second side 38 so that movement of either of the buttons 97, 99 from the first to the second positions relative to the locking member 28 will pivotally move the associated release arm 92 or 94 from the disengaged to the engaged position and thus drives the lever lock 84 from the latched position to the unlatched position.

The dual-sided lever lock release assembly 80 includes biasing means for biasing the lever lock 84 axially toward the latched position in the form of a coil spring 96 connected to handle part 18 of the elongate locking member 28 and to one end of the base portion 82 of the lever lock 84. The coil spring 96 is placed in tension to bias the lever lock 84 toward the latched position. The biasing means may comprise any suitable means including but not limited to a leaf spring, a coil spring, an extension spring, a compression spring or a torsion spring.

The hook portion 86 comprises camming surface 89 adapted to engage the surfaces defining the slot 83 of the second structural member 14 when the elongate locking member 28 is moved from the release to the locking positions. The camming surface 89 moves the lever lock 84 from the latched position to the unlatched position against the bias of the coil spring 96 to afford passage of the hook portion 86 from one side of the slot 83 in the second structural member 14 to the other to thereby afford engagement between the retaining surface 87 of the hook portion 86 and the surfaces of the second structural member 14 surrounding the slot 83 when the elongate locking member 28 is moved from the release position (FIG. 3) to the locking position (FIG. 2). The coil spring 96 biases the lever lock 84 axially toward the latched position and thus causes a tactile "click" when the lever lock 84 slides to the latched position and the retaining surface 87 engages the surfaces surrounding the slot 83.

The second structural member 14 is adapted to have an elongate fixed or removable anvil 40 positioned over and along the jaw part 22 to form the first assembly 11, and the jaw part 20 of the first structural member 12 has an elongate channel or groove 39 adapted to receive a cartridge body 41 of the improved cartridge assembly 2 according to the present invention to form the second assembly 13. Alternatively, the cartridge body 41 may be intergral with the first structural member 12.

The cartridge body 41 contains a plurality of staples 43 disposed in rows oriented longitudinally of the jaw part 20 in opposition to the anvil 40 when the structural members 12, 14 are in their closed position. Another feature of the present invention which distinguishes the cartridge assembly 2 from existing cartridge assemblies includes an adjustable handle assembly, generally designated by the reference number 50. The cartridge assembly 2 includes manually actuatable means including cam-like drivers or pushers 45 having first 44 and second 44A longitudinally spaced end portions. The pushers 45 are adapted to move longitudinally along the first jaw part 20 with the second end portion 44A sequentially pressing the staples 43 against the anvil 40 to engage and close the staples 43 in tissues between the jaw parts 20, 22 with the first end portion 44 moving between the handle part 16 and the base portion 8. The pushers 45 are adapted to be moved through longitudinal slots in the cartridge body 41 by manually pressing on the adjustable firing handle assembly 50.

The adjustable firing handle assembly 50 is connected to the first end portions 44 of the pushers 45. When the adjustable firing handle assembly 50 is manually pressed to move the firing body 52 from the pre-fired position (FIG. 2) to the fired position, the drivers or pushers 45 sequentially eject the staples 43 from the cartridge body 41 by means of camming plungers 47 under the staples 43. The camming plungers 47 push the staples 43 toward a surface of the cartridge body 41 opposite the anvil 40 and thereby press the ejected staples 43 against specially shaped surfaces on the anvil 40 to engage and close the staples 43 in tissues between the jaw parts 20, 22 when the structural members 12, 14 are in their closed position. The cartridge assembly 42 can also optionally include a knife (not shown) that is also connected to the firing body 52 adjacent the pushers or drivers 45 so that manual movement of the pushers or drivers 45 to eject and close the staples 43 also moves the knife along the jaw parts 20, 22 with the distal end of the knife in a slot (not shown) in the anvil 40 to cut tissues between parallel, spaced rows of applied staples 43.

The adjustable firing handle assembly 50 comprises the elongate firing body 52 within a space 27 between the handle part 16 of the first structural member 12 and the base portion 8 of the second structural member 14 for moving the pushers 45 from the retracted (FIGS. 2) to the extended positions. The elongate firing body 52 has a longitudinal axis L (FIG. 6) transverse to the direction in which the structural members 12, 14 are elongate. The firing body 52 has opposite first 53 and second 55 end portions. A firing handle adapter 58 is attached to the first end portions 44 of the pushers 45 and is adapted to connect the elongate firing body 52 to the pushers 45.

A means 60 is provided which mounts the elongate firing body 52 to the firing handle adapter 58 for releasable, reciprocating lateral movement of the elongate firing body 52 along the longitudinal axis L in the form of a rod 61 extending between end portions 53 and 55 and located within an opening 69 in the firing handle adapter 58. A detent means 62 is also provided which releasably secures the elongate firing body 52 in a first position (FIG. 6) with the first end portion 53 of the elongate firing body 52 generally adjacent a first side 19 of the structural members 12, 14 and a second position (FIG. 5, solid lines) with the second end portion 55 of the elongate firing body 52 generally adjacent a second side 21 of the structural members 12, 14.

The structural members 12, 14 have an axis A (FIGS. 5 and 6) extending generally in the first direction along a middle portion of the stapler 10. The detent means 62 also releasably positions the firing body 52 at a middle position (FIG. 5, dashed lines) midway between the first and second positions at which parts of the first and second portions 53 and 55 of the firing body 52 project beyond both the first and second sides 19, 21. When the elongate firing body 52 is placed in the middle position, the end portions 53 and 55 are located laterally beyond the sides 19', 21' of the elongate locking member 28 and provide surfaces on both sides of the stapler 10 for manually pressing on the elongate firing body 52.

Rectangular side walls 56 are included in the elongate firing body 52 and cooperate with the first and second end portions 53, 55 to form a rectangular box-shape 64 open along the side walls 56 into a cavity 59. The elongate firing body 52 has inside 65 and outside 67 surfaces, and the detent means 62 include a detent surface 68 which extend beyond the inside surface 65 of one of the rectangular side walls 56. It should be noted that the firing body 52 may comprise any suitable shape including, but not limited to square, triangular, arcuate and combinations of those shapes.

The firing handle adapter 58 has a neck portion 70 having first 72 and second 74 opposite generally planar flank walls, and surfaces which define a notch 76 adapted to receive the detent surface 68 of the elongate firing body 52. As shown in FIG. 4, the neck portion 70 is adapted to extend into the cavity 59 of the firing body 52.

The first and second opposite planar flank walls 72, 74 are releasably secured between the detent surface 68 and the inner surface 65 of the second end portion 55 of the elongate firing body 52 when the elongate firing handle body 52 is in the first position, and the first and second opposite planar flank walls 72, 74 are releasably secured between the detent surface 68 and the inner surface 65 of the first end portion 53 of the elongate firing body 52 when the elongate firing handle body 52 is in the second position.

The means 60 mounting the elongate firing handle body 52 to the firing handle adapter for reciprocating manual movement of the firing body 52 along its longitudinal axis L comprises the cylindrical pin or rod 61 attached at its ends to the end portions 53, 55 of the firing body 52, and the neck portion 70 of the adapter 58 having surfaces defining an opening 69 adapted to receive the cylindrical pin 61.

In the middle position (FIG. 5, dashed lines), the detent means 62 mounts the firing body 52 to the firing handle adapter 58 with the detent surface 68 engaged with the notch 76 of the neck portion 70 and with the first 53 and second 55 end portions of the firing body 52 generally equidistant from the axis A of the stapler 10. As shown in FIG. 5, in the middle position, parts of the first and second end portions 53, 55 project beyond both the first and second sides 19, 21 of the structural members 12, 14.

The side wall 56 of the firing body 52 proximate the user includes flared edges 57 near the end portions 53, 55. The flared edges 57 provide means for grasping the firing body 52 with, for example, the user's thumbs and are flared outward to deter the user's thumbs from sliding laterally off the firing body 52. The flared edges 57 also deter the detent surface 68 from disengaging the notch 76 when the firing body 52 is in the middle position as manual pressure on the firing handle body 52 only increases the engagement between the notch 76 and the detent surface 68. The side wall proximate the user also includes a plurality of ribs 66 which assist the flared edges 57 in retaining the user's digit on the firing body 52 by providing additional friction surfaces.

During use of the stapler 10, the engagement surfaces 24 of the handle cover 328 and the handle cover 15 may be engaged by the fingers of a user's hands while the user's thumb is used to operate the adjustable firing body 52. The user may use only one hand to operate the firing body 52 when the firing body 52 is in the first or second positions. Such a feature is desirable for user's who prefer to exclusively use either their right or left hand when firing the stapler. When the firing body 52 is in the middle position, however, both of the user's thumbs may be used to operate the projecting parts of the firing body 52 to afford symmetrical manual pressing on the firing body 52 about the axis A of the first and second structural members 12, 14. Affording a user the capacity to symmetrically press on the firing body 52 from both sides of the axis A of the first and second structural members 12, 14 assists the user in controlling the position and stability of the stapler 10 and provides more effective firing of the stapler 10 when it is used, for example, in procedures which require a relatively large force to move the firing body 52 from the pre-fired to the fired position.

The present invention has now been described with reference to several embodiments thereof. It will be apparent to those skilled in the art that many changes or additions can be made in the embodiments described without departing from the scope of the present invention. For example, the elongate firing handle body 52 may include a close friction fit with the firing handle adapter 58 thereby replacing the detent 68. Also, the elongate firing handle body 52 need not reciprocate or shuttle between the sides of the stapler 10 and may instead comprise only a single, fixed body which extends on both sides 19, 21 of the stapler 10. Also, the firing handle body may comprise a pivotal cantilever member which is pivotal between the sides of the stapler 10 in order to provide means for firing the stapler from either side 19 or 21. Thus, the scope of the present invention should not be limited to the structures described in this application, but only by structures described by the language of the claims and the equivalents of those structures.

We claim:

1. A surgical stapler having:

first and second structural members each being elongate in a first direction, the first structural member having a handle part including first and second ends and the second structural member having a base part having first and second ends, and each of the first and second structural members having a jaw part projecting from said first ends, said structural members having pivot means at said second ends adapted for free engagement and disengagement in a plane normal to said first direction for affording, when engaged, relative pivotal movement of said structural members in said plane between a closed position with said jaw parts in closely spaced relationship, and an open position with said jaw parts spaced farther from each other than in said closed position;

an elongate locking member having first and second ends, first and second sides, inner and outer surfaces extending between said sides and a pivot point closely adjacent the first end of the locking member, the pivot point of said locking member being mounted on said second structural member adjacent the first end of said second structural member for pivotal movement around an axis generally normal to said first direction between a locking position generally aligned with the handle part of said second structural member with said inner surface adjacent said second structural member, and a release position with the second end of said locking member spaced from the second end of said second structural member, said first end of said locking member and said handle part of said first structural member adjacent the first end of said first structural member having surfaces adapted, when said pivot means are engaged with said structural members in said open position, for engagement during movement of said locking member from said release position to said locking position to forcefully move said structural members to said closed position; and means for releasable engagement between the elongate locking member and the second structural member comprising said second structural member having a slot extending between said inner and outer surfaces generally adjacent the second end of said second structural member;

a lever lock including a hook portion adapted to pass through said slot in said second structural member and having a retaining surface adapted to engage a portion of said inner surface, means for mounting the lever lock on said locking member for movement between an unlatched position with said hook portion aligned to pass through said slot and to afford movement of the locking member between said latched and release positions and an latched position with said hook portion aligned to position the retaining surface along a portion of said inner surface to retain the elongate locking member in the locking position;

first and second release buttons; and actuating means mounting said first and second release buttons on opposite sides of said locking member for movement between first and second positions with respect to said locking member, said actuation means being operable by movement of either of said buttons from said first to said second positions for moving said lever lock from said engaged position to said disengaged position.

2. A surgical stapler according to claim 1 wherein said lever lock further includes biasing means adapted to bias said hook portion toward said latched position, and said hook portion includes a camming surface adapted to engage a surface defining said slot in said second structural member to move said lever lock against the bias of said biasing means from said latched position to said unlatched position to afford movement of said hook portion through said slot when said locking member moves from said release to said locking position, said biasing means causing movement of the lever lock from said unlatched position to said latched position when said locking member is positioned at said locking position.

3. A surgical stapler according to claim 1 wherein said actuation means includes first and second release arms each having first and second ends, said second ends including camming surfaces adapted to engage said shoulder portion of said hook portion, and each of said first ends being pivotally attached to said elongate locking member for pivotal movement of each of said release arms between an engaged position with said camming surface engaged with said shoulder portion of said hook portion to drive said lever lock from said latched position to said unlatched position to afford movement of the locking member to said release position and a disengaged position with said camming surface of said release arm positioned with respect to said shoulder surface of said hook portion, said first button being mounted on said first release arm between said pivot and said camming surface, and said first button being positioned along one side of said locking member, and said second button being mounted on said second release arm between said pivot and said camming surface, said second button being positioned along the other side of said locking member, said cam surfaces being disposed so that movement of either of said buttons from an outer to an inner position relative to said locking member will drive said lever lock from said latched position to said unlatched position.

4. In combination, a stapler firing assembly and a surgical stapler having:

first and second structural members each being elongate in a first direction, the first structural member having a handle part including first and second ends and the second structural member having a base part having first and second ends, and each of the first and second structural members having a jaw part projecting from said first ends, said first and second structural members having first and second sides, an anvil positioned along the first jaw part, and a plurality of staples positioned along the second jaw part in opposition to the anvil, said structural members having pivot means at said second ends adapted for free engagement and disengagement in a plane normal to said first direction for affording, when engaged, relative pivotal movement of said structural members in said plane between a closed position with said jaw parts in closely spaced relationship, and an open position with said jaw parts spaced farther from each other than in said closed position;

an elongate locking member having first and second ends, first and second sides, inner and outer surfaces extending between said sides and a pivot point closely adjacent the first end of the locking member, the pivot point of said locking member being mounted on said second structural member adjacent the first end of said second structural member for pivotal movement around an axis generally normal to said first direction between a locking position generally aligned with the handle part of said second structural member with said inner surface adjacent said second structural member, and a release position with the second end of said locking member spaced from the second end of said second structural member, said first end of said locking member and said handle part of said first structural member adjacent the first end of said first structural member having surfaces adapted, when said pivot means are engaged with said structural members in said open position, for engagement during movement of said locking member from said release position to said locking position to forcefully move said structural members to said closed position; and means for releasable engagement between the elongate locking member and the second structural member comprising:

said second structural member having a slot extending between said inner and outer surfaces generally adjacent the second end of said second structural member, a lever lock including a hook portion adapted to pass through said slot in said second structural member and having a retaining surface adapted to engage a portion of said inner surface, means for mounting the lever lock on said locking member for movement between an unlatched position with said hook portion aligned to pass through said slot and to afford movement of the locking member between said latched and release positions and an latched position with said hook portion aligned to position the retaining surface along a portion of said inner surface to retain the elongate locking member in the locking position, first and second release buttons; and actuating means mounting said first and second release buttons on opposite sides of said locking member for movement between first and second position with respect to said locking member; said actuation means being operable by movement of either of said buttons from said first to said second positions for moving said lever lock from said engaged position to said disengaged position, said stapler firing assembly comprising:

a pusher having a longitudinal axis and first and second longitudinally spaced end portions, said pusher being adapted to move longitudinally along the second jaw part with said second end portion sequentially pressing the staples against the anvil to engage and close the staples in tissues between the jaw parts with said first end portion moving between said handle parts, a firing handle body having opposite end portions;

means mounting said handle body on the first end portion of said pusher for movement relative to said pusher between a first position at which one of said end portions projects from the first side of said structural members, and a second position at which one of said end portions projects from the second side of the structural members so that the firing handle body can be positioned to be manually engaged on either side of the structural members to move the second end of the pusher along the second jaw to eject and close the staples.

* * * * *

UNITED STATES PATENT AND TRADEMARK OFFICE
CERTIFICATE OF CORRECTION

PATENT NO. : 5,083,695
DATED : January 28, 1992
INVENTOR(S) : Foslien et al

It is certified that error appears in the above-indentified patent and that said Letters Patent is hereby corrected as shown below:

Col. 11, line 51, "handle part" should read --base part--.

Col. 13, lines 13-14, "first jaw" should read --second jaw--.

Col. 13, line 15, "second jaw" should read --first jaw--.

Col. 13, line 34, "handle part" should read --base part--.

Col. 14, line 23, "position" should read --positions--.

Col. 14, line 26, "positions" should read --position--.

Col. 14, line 33, "second jaw" should read --first jaw--.

Col. 14, line 37, "handle parts" should read --structural members--.

Col. 14, line 49, "second" should read --first--.

Signed and Sealed this

Twenty-fourth Day of August, 1993

Attest:

BRUCE LEHMAN

Attesting Officer

Commissioner of Patents and Trademarks